United States Patent [19]

Bianchi et al.

[11] Patent Number: 5,229,280
[45] Date of Patent: Jul. 20, 1993

[54] PROCESS FOR THE CONTINUOUS BIOTECHNOLOGICAL PREPARATION OF OPTICAL ISOMER S(+) OF 2-(6-METHOXY-2-NAPHTHYL) PROPIONIC ACID

[75] Inventors: Daniele Bianchi, Milan; Pietro Cesti, Trecate; Carlo Pina, Milan; Ezio Battistel, La Spezia, all of Italy

[73] Assignee: Istituto Guido Donegani S.p.A., N Ovara, Italy

[21] Appl. No.: 312,976

[22] Filed: Feb. 21, 1989

[30] Foreign Application Priority Data

Feb. 25, 1988 [IT] Italy .............................. 19532 A/88
Jul. 29, 1988 [IT] Italy .............................. 21558 A/88

[51] Int. Cl.$^5$ ..................... C12N 11/08; C12N 9/20; C12N 9/18; C12P 41/00
[52] U.S. Cl. ..................... 435/136; 435/180; 435/197; 435/198; 435/280; 435/921
[58] Field of Search ............. 435/136, 180, 280, 197, 435/198, 921

[56] References Cited

U.S. PATENT DOCUMENTS

| | | |
|---|---|---|
| 3,663,467 | 5/1972 | Albright . |
| 3,891,412 | 6/1975 | Bhakshanker . |
| 4,146,432 | 3/1979 | Hirohara et al. ............ 435/180 |
| 4,762,793 | 8/1988 | Cesti et al. ............ 435/280 |
| 4,818,695 | 4/1989 | Eigtved ............ 435/180 |
| 4,857,462 | 8/1989 | Maier et al. ............ 435/280 |
| 4,886,750 | 12/1989 | Bertola et al. ............ 435/136 |
| 4,897,352 | 1/1990 | Chonde et al. ............ 435/180 |
| 4,898,822 | 2/1990 | Asada et al. ............ 435/136 |

FOREIGN PATENT DOCUMENTS

227078 7/1987 European Pat. Off. .
89/02916 4/1989 World Int. Prop. O. .

OTHER PUBLICATIONS

Biotechnology and Engineering, vol. 38, pp. 659–664 (1991), "Enzymatic Resolution of (S)-(+)-Naproxen in a Continuous Reactor", Battistel, et al.
Biotechnology and Bioengineering, vol. 22, pp. 735–756 (1980), "Kinetic Behavior of Immobilized Penicillin Acylase", Carleysmith, et al.

*Primary Examiner*—Herbert J. Lilling
*Attorney, Agent, or Firm*—Morgan & Finnegan

[57] ABSTRACT

Continuous biotechnological preparation of optical isomer S(+) of 2-(6-methoxy-2-naphthyl) propionic acid consisting in the reaction of a racemic (R,S) ester of 2-(6-methoxy-2-naphthyl) propionic acid having melting point below 50° C. of formula:

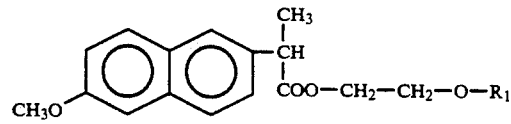

wherein
$R_1$ = a $C_2$-$C_{10}$ alkyl, $C_4$-$C_6$ cycloalkyl, phenyl, tetrahydropyranyl, tetrahydrofuranyl radicals and —(CH$_2$CH$_2$O)$_n$—$R_2$ group, wherein n = 2–15 and
$R_2$ = a $C_1$-$C_4$ alkyl group, with the Lipase obtained from *Candida Cylindracea*, at temperatures ranging from 20°–60° C. and at a pH ranging from 5 to 8, by feeding said ester in a continuous way into a bioreactor containing said Lipase immobilized on a porous carrier selected from adsorbent resins of the polyacrylester type having a porosity ranging from 50 to 1000 Å and a granulometry ranging from 1 to 0.01 mm.

7 Claims, 1 Drawing Sheet

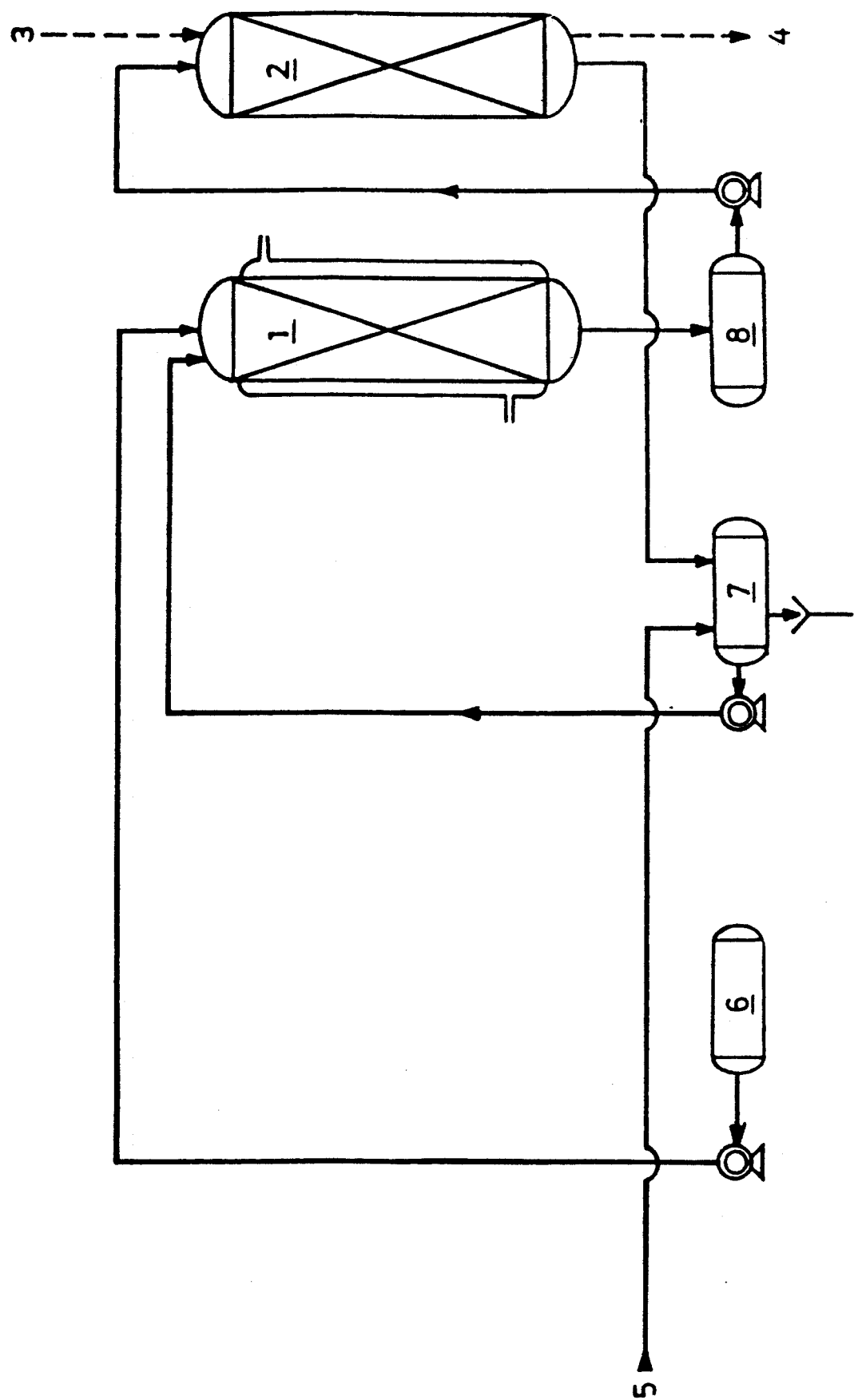

PROCESS FOR THE CONTINUOUS BIOTECHNOLOGICAL PREPARATION OF OPTICAL ISOMER S(+) OF 2-(6-METHOXY-2-NAPHTHYL) PROPIONIC ACID

DESCRIPTION OF THE INVENTION

The present invention relates to an improved process for the continuous biotechnological preparation of optical isomer S(+) of 2-(6-methoxy-2-naphthyl) propionic acid (NAPROXEN®), starting from particular racemic (R,S) esters of 2-(6-methoxy-2-naphthyl) propionic acid having melting point below 50° C.

It is known, for instance from T. Y. Shen, Angew. Chem., Int. Ed. Engl., 11, 460, 1972, that 2-(6-methoxy-2-naphthyl) propionic acid is used as a non-steroidal antiinflammatory agent. Said acid, having a center of asymmetry in the α position, is present in two S(+) and R(−) enantiomeric forms which are optically active.

It is also known from the above-mentioned article that the anti-inflammatory activity of enantiomer S(+) is about 20 times higher than the anti-inflammatory activity of enantiomer R(−). Therefore it was desirable to separate enantiomer S(+) from less active enantiomer R(−).

In European patent application No. 195,717 a process is disclosed for the biotechnological separation of optical isomer S(+) from optical isomer R(−) of 2-(6-methoxy-2-naphthyl) propionic acid by stereoselective enzymatic hydrolysis of suitable racemic (R,S) esters of said acid, having the formula:

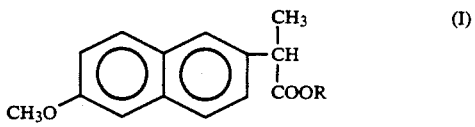

wherein R is selected from:
—CH$_2$—C≡CH, —CH$_2$—CH=CH$_2$, —CH$_2$—CN, —CH$_2$COCH$_3$, —CH$_2$COO—C$_1$-C$_4$ alkyl radical, and —CH$_2$—CH$_2$—O—C$_1$-C$_4$ alkyl radical.

As enzyme, use is made preferably of the Lipase produced by microorganism *Candida Cylindracea* (ATCC No. 14830), which is capable of hydrolyzing selectively optical isomer S(+) of the racemic ester having formula (I), while leaving the ester in the R(−) form substantially unchanged.

The above-mentioned process, however, turns out to be scarcely suitable for an economical industrial realization because the enzyme loses about 80% of its activity after having reacted over 96 hours, and therefore it cannot be used again for further stages of hydrolysis or it cannot be used again in a continuous hydrolysis process, with the achievement of high productivities in hydrolyzed product per unit of enzyme, that has been used.

In accordance with the present invention, it has now been discovered that the continuous hydrolysis process can be carried out with achievement of high productivities in hydrolyzed product, while keeping the enzyme activity practically unchanged over long periods of time, if use is made of particular racemic esters of 2-(6-methoxy-2-naphthyl) propionic acid, having melting point below 50° C. and if the enzyme obtained from *Candida Cylindracea* is used after having been immobilized on particular porous carriers selected from the absorbent resins with polyacrylester matrix, having a porosity ranging from 50 to 1000 Å and a granulometry ranging from 1 to 0.01 mm.

In fact, it has been verified that if use is made of other porous carriers having a porosity and granulometry within the above-mentioned ranges, but having a nature which differs from that of polyacrylester, only low conversions are achieved of the racemic ester into the hydrolyzed product, and therefore the continuous process of enzymatic hydrolysis cannot be carried out profitably.

Therefore the object of the present invention consists in a continuous process for the biotechnological preparation of optical isomer S(+) of 2-(6-methoxy-2-naphthyl) propionic acid, consisting in the reaction of a racemic (R,S) ester of 2-(6-methoxy-2-naphthyl) propionic acid, having melting point below 50° C., of formula:

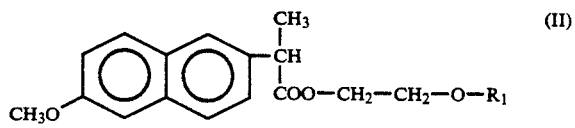

wherein R$_1$ is selected from the group consisting of alkyl radicals having from 2 to 10 carbon atoms, cycloalkyl radicals having from 4 to 6 carbon atoms, phenyl, tetrahydropyranyl, tetrahydrofuranyl radicals, and a —(CH$_2$CH$_2$O)$_n$—R$_2$ group, wherein n is a number ranging from 2 to 15 and R$_2$ is an alkyl radical having from 1 to 4 carbon atoms, with the Lipase obtained from *Candida Cylindracea*, at temperatures ranging from 20° to 60° C. and at a pH ranging from 5 to 8, and in recovering said acid S(+), characterized in that said ester is fed in a continuous way, together with a phosphate buffer solution, into a column bioreactor filled with said Lipase immobilized on a porous carrier selected from adsorbent resins consisting of polymers of acrylic ester having a porosity ranging from 50 to 1000 Å and a granulometry ranging from 1 to 0.01 mm, wherein the ratio by weight Lipase/carrier ranges from 1:2 to 1:10, and in separating said acid in the S(+) form from the reaction mixture according to known methods.

The Lipase produced by microorganism *Candida Cylindracea* ATCC 14830 is an enzyme, which is on sale with different degrees of purity and can be obtained from cultures of the microorganism according to customary procedures.

As carriers, according to this invention, use may be made of adsorbent resins whose polymeric matrix consists of polyacrylic esters having a porosity ranging from 50 to 1000 Å and a granulometry ranging from 1 to 0.01 mm, capable of adsorbing both Lipase and racemic ester of formula (II), such as, for instance AMBERLITE ® XAD 8 and AMBERLITE ® XAD 7 resins.

The immobilization of the Lipase on the carrier may be achieved by simple mixing, under stirring, of the carrier with an aqueous solution, buffered at a pH ranging from 6 to 8, of the Lipase, by using ratios Lipase/carrier ranging from 1:2 to 1:10.

Moreover a still more stable fixing of the Lipase on the carrier may be obtained by bringing the supported Lipase into contact with an aqueous solution of a polyvalent aldehyde, and in particular a saturated aliphatic dialdehyde having from 2 to 10 carbon atoms, such as, for instance, glutaraldehyde.

The bioreactor arrangement generally consists essentially of a thermoregulated column, having a diameter/- length ratio ranging from 1:3 to 1:50, filled with the carrier, containing the Lipase that has been immobilized.

The starting racemic (R,S) esters having formula (II) may be prepared according to conventional esterification processes from racemic 2-(6-methoxy-2-naphthyl) propionic acid for instance according to the following reaction:

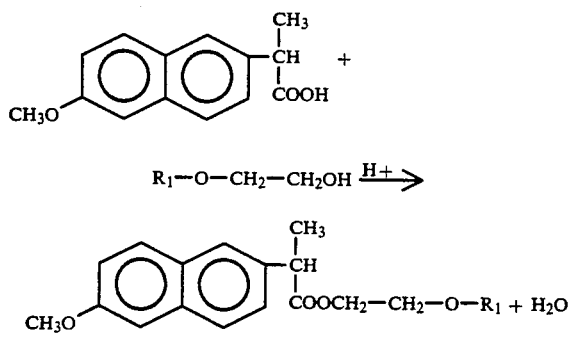

wherein $R_1$ has the meaning already defined herein.

Among the racemic (R,S) esters of formula (II), the esters wherein $R_1$ represents a $C_2-C_4$ alkyl radical, in particular ethoxyethylester, n-propoxyethylester, isopropoxyethylester and n-butoxyethylester of racemic 2-(6-methoxy-2-naphthyl) propionic acid, have turned out to be preferred.

The aqueous solution of phosphate buffer is used at different molarities of $Na_2HPO_4$ and $KH_2PO_4$, in order to keep the pH at the pre-established value during the hydrolysis reaction and to dissolve, in the form of a salt, the S(+) 2-(6-methoxy-2-naphthyl) propionic acid produced by hydrolysis.

The hydrolysis reaction is carried out preferably at temperatures ranging from 30° to 50° C. and at a pH ranging from 6 to 7.

According to a preferred embodiment of the invention, the column bioreactor filled with the Lipase immobilized on the carrier and thermoregulated at a temperature ranging from 20° to 60° C., is fed at the start with a continuous flow of (R,S) ester having formula (II), until complete saturation of the carrier. The ratio by weight between the amount of adsorbed ester in the bioreactor and the amount of filling carrier generally ranges from 1:2 to 1:20.

The column, after having been saturated, is fed in a continuous way with a flow of 0.15 N-phosphate buffer, pH 6.5, and with a parallel flow of the aforesaid racemic ester, in a ratio by volume ester/buffer solution generally ranging from 1:50 to 1:200.

The flow of racemic ester displaces continuously from the column the ester enriched with the optical isomer R(—) which has not been hydrolyzed by the Lipase.

At the outlet of the bioreactor one obtains a suspension of the ester having formula (II) enriched with the optical isomer R(—) in an aqueous buffer solution containing 2-(6-methoxy-2-naphthyl) propionic acid, prevailingly in the form of the optical isomer S(+) and the corresponding ether of the ethylene glycol produced during hydrolysis.

Acid and ester may be extracted from the mixture leaving the bioreactor, after acidification, by using organic solvents immiscible with water, such as, for instance, methylene chloride, toluene, ethyl ether and the like.

From the organic extract thus obtained and subsequently concentrated, the acid, substantially in the S(+) form, is then separated from the ester enriched with the R(—) form, by passing the extract onto a chromatographic column, by using, for instance, silica gel as the stationary phase.

Alternatively the acid, substantially in the S(+) form, may be isolated by extraction from the organic extract by means of basic washings, for instance with aqueous solutions of NaOH at 5% by weight or of KOH at 10% by weight.

According to still another embodiment, acid and ester are separated from the mixture leaving the bioreactor by passing said mixture into a second column filled with adsorbent resins, for instance of AMBERLITE ® XAD 7 or AMBERLITE ® XAD 4 type, where acid and ester are adsorbed on the resin and where at the outlet of the adsorption column, the buffer solution is obtained containing the corresponding ether of ethylene glycol.

Subsequently acid and ester are extracted from the adsorption column by means of washings with an organic solvent miscible with water, such as, for instance, methanol or ethanol.

Then from the organic extract, thus obtained and subsequently concentrated, the acid, substantially in the S(+) form, is separated from the ester enriched with the R(—) form, according to the methods described above.

The buffer solution containing glycol, obtained at the outlet of the adsorption column, after having been brought to the starting pH of 6.5 by means of an aqueous solution of KOH, is then recycled into the bioreactor.

Such buffer solution may be recycled until the glycol concentration is not over 10% by weight, as higher concentrations in glycol would cause phenomena involving hydrolysis inhibition.

The ester enriched with the R(—) form, after having been separated as explained above, may then be subjected to racemization by treatment with a base in an anhydrous medium, and subsequently recycled into the bioreactor.

A few examples follow by way of illustration of the invention, but without limiting its scope.

EXAMPLE 1

Immobilization of the Enzyme 500 g of AMBERLITE ® XAD 7 resin were washed with a liter of methanol and then conditioned with a solution of 0.15 N phosphate buffer pH 6.5.

The resin was added to a solution of 100 g of Lipase obtained from *Candida Cylindracea* (Sigma L 1754 type VII, 500 u/mg) in a liter of phosphate buffer pH 6.5 (0.15 N) and stirred in a shaker at 200 rpm for 24 hours, at room temperature.

The resin was filtered and washed with a liter of phosphate buffer pH 6.5.

Then the reaction of hydrolysis and subsequent separation of the acid from the reaction mixture was carried out by using the apparatus according to the accompanying FIG. 1.

In FIG. 1, (1) represents the bioreactor consisting of a thermoregulated column containing the supported Lipase, (2) the adsorption column, (3) the feeding of the washing organic solvents, (4) the organic extract leaving the adsorption column, (5) the feeding of the fresh buffer solution, (6) the feeding reservoir of the racemic ester, (7) the reservoir for collecting the fresh and recycled buffer solutions, (8) the reservoir for collecting the reaction mixture after hydrolysis.

Continuous Hydrolysis Process

Referring to FIG. 1, the carrier, containing the immobilized enzyme as described above, was pressed into bioreactor (1) consisting of a thermoregulated column having a diameter of 5 cm and a height of 60 cm.

The column was then fed by a flow of racemic ethoxyethyl-[2-(6-methoxy-2-naphthyl)] propionate until complete saturation of the resin.

The carrier absorbed 490 g of racemic ester.

The column was thermoregulated at 35° C. and fed with a flow of 7.2 ml/h of racemic ethoxyethyl-[2-(6-methoxy-2-naphthyl)] propionate and with a parallel flow of 800 ml/h of phosphate buffer pH 6.5 (0.15 N).

The mixture leaving the column consisted of a suspension of ester enriched with the R(−) form in a solution of 2-(6-methoxy-2-naphthyl) propionic acid in the S(+) form and ethylene glycol monoethylether.

Separation of S(+) 2-(6-methoxy-2-naphthyl) propionic acid from the reaction mixture The reaction mixture leaving bioreactor (1) was fed in a continuous way into adsorption column (2) having a diameter of 5 cm and a height of 60 cm, thermoregulated at 20° C. and containing 500 g of pressed AMBERLITE ® XAD 4.

Such column was capable of absorbing both 2-(6-methoxy-2-naphthyl)-propionic acid and ethoxyethyl-[2-(6-methoxy-2-naphthyl)]-propionate.

At the outlet of the adsorption column one obtained a phosphate buffer solution containing ethylene glycol monoethylether, formed during the enzymatic hydrolysis. Such a solution was brought again to pH 6.6 by addition of NaOH and was recycled to feed bioreactor (1) with the concentration of ethylene glycol monoethylether remaining below 5%.

The adsorption column reached saturation after having worked over a period of 40 hours then was regenerated.

The regeneration was carried out by washing the adsorption column with 10 liters of methanol, fed with a flow of 850 ml/h at a temperature of 35° C.

When the washing was over, column (2) was conditioned again by means a flow of 5 liters of phosphate buffer pH 6.5 (0.15 N), and was connected again with the effluent from bioreactor (1).

In order to render the process continuous, use was made in practice of two adsorption columns working by turns.

The 10 liters of methanolic solution coming from each washing of the adsorption columns were evaporated at reduced pressure; the residue, consisting of the acid in the S(+) form and of the ester enriched with the R(−) form, was dissolved again in 2 liters of ethyl acetate and extracted with 2 liters of NaOH at 5%.

The aqueous solution was brought to pH 1 by the addition of HCl at 10% whereupon the acid precipitated in the S(+) form, which was separated by filtration and dried in an oven at 100° C.

The organic phase containing the ester enriched with the R(−) form, after dehydration by means of sodium sulphate and evaporation of ethyl acetate, was conveyed to the racemization phase, which will be described below.

From each washing cycle of the adsorption column, an amount of S(+) 2-(6-methoxy-2-naphthyl) propionic acid, ranging from 60 to 70 g was obtained, having the following characteristics: m.p. 154°-5° C., $[\alpha]_D^{20}$ (C=1, CHCl$_3$)+66.4°, $^1$H-NMR (90 MHz in CDCl$_3$) (ppm) : 1.57 (3H, d, —CHCH$_3$), 3.83 (1H, q, CH), 3.86 (3H, s, OCH$_3$), 6.9–8.0 (6H, m, arom.), 8.0 (1H, s broad, OH), plus an amount of ethoxyethyl-[2-(6-methoxy-2-naphthyl)] propionate enriched with the R(−) form ranging from 260 to 280 g.

By operating under the conditions as described above, the system shown in FIG. 1, fed over 1200 hours of continuous running with 9387 g of racemic ethoxyethyl-[2-(6-methoxy-2-naphthyl)] propionate, yielded 1757 g of S(+) 2-(6-methoxy-2-naphthyl) propionic acid with a conversion of 25%, having m.p. 154°-5° C. and $[\alpha]_D^{20}$ (C=1, CHCl$_3$), +66.3°, and 7050 g of ester enriched with the R(−) form, without showing any perceptible decrease in effectiveness and productivity.

Racemization of Ethoxyethyl-2-(6-Methoxy-2-Naphthyl)] Propionate 314 g of ethoxyethyl-[2-(6-methoxy-2-naphtyl)] propionate enriched, with the R(−) form, were added to a mixture of 300 ml of ethylene glycol monoethylether and 36 ml of a solution of KOH at 10%.

The mixture was heated to reflux over 5 hours.

When the reaction was over ($[\alpha]_D^{20}$ 0°) the ethylene glycol monoethylether was evaporated, treated with 1 liter of ethyl acetate, washed 3 times with 1 liter of water, and dehydrated on sodium sulphate. After evaporation of the solvent, 298 g of racemic ethoxyethyl-[2-(6-methoxy-2-naphthyl)] propionate were obtained, with a yield of 95%.

EXAMPLE 2

1 g of Lipase obtained from *Candida Cylindracea* (Meito Sangyo OF-360, 360,000 u/g) was immobilized on 25 g of AMBERLITE ® XAD 7 resin, as described above in Example 1.

Then the resin was pressed into a bioreactor consisting of a thermoregulated column having a diameter of 3 cm and a height of 30 cm.

The column was saturated with racemic ethoxyethyl-[2-(6-methoxy-2-naphthyl)] propionate and then fed with a flow of 0.3 ml/h of the same ester and 31 ml/h of phosphate buffer pH 6.5 (0.15 N) at 35° C.

The mixture leaving the column was conveyed into a second adsorption column having a diameter of 3 cm and a height of 30 cm.; filled with 50 g of pressed AMBERLITE ®XAD 4.

At the outlet of the second column one obtained a buffer solution which was recycled to feed the column bioreactor, after having been brought again to a pH of 6.5, by the addition of NaOH.

The acid in the S(+) form and the ester enriched with the R(−) form were extracted from the adsorption column and separated according to the same procedure as described above in Example 1.

By operating under the conditions set forth above, the system, fed in a continuous way over 500 hours with 146 g of racemic ester, yielded 34 g of S(+) 2-(6-methoxy-2-naphthyl) propionic acid with a conversion of 31%, having m.p. 154°-5° C. and $[\alpha]_D^{20}$ (C=1, CHCl$_3$), +65.9°, and 101 g of ethoxyethyl-[2-(6- methoxy-2-naphthyl)] propionate enriched with the R(−) form.

EXAMPLE 3

1 g of Lipase obtained from *Candida Cylindracea* (Meito Sangyo OF-360, 360,000 u/g) was immobilized on 25 g of AMBERLITE ® XAD 8, by using the same procedure as described above in Example 1.

The immobilized enzyme was then introduced into a bioreactor consisting of a column having a diameter of 3 cm and a height of 30 cm, fed as described above in Example 2.

By operating under these conditions the system was fed in a continuous way over 500 hours with 146 g of racemic ester, thereby obtaining 40 g of S(+) 2-(6-methoxy-2-naphthyl) propionic acid with a conversion of 37%, having m.p. 154°-5° C. and $[\alpha]_D^{20}$ (C=1, CHCl$_3$), +67.1°, and 91 g of ethoxyethyl-[2-(6-methoxy-2-naphthyl)] propionate enriched with the R(−) form.

EXAMPLE 4

A test of continuous enzymatic hydrolysis was carried out by using the same apparatus and by operating under the same conditions as described in Example 1, while replacing racemic ethoxyethyl-[2-(6-methoxy-2-naphthyl)] propionate, with racemic n-propoxyethyl2-(6-methoxy-2-naphthyl) propionic acid keeping in mind, however, that in this case the carrier of column 1 absorbed at the start 480 g of racemic ester instead of 490 g and that, from the enzymatic hydrolysis, ethylene glycol monopropylether formed, instead of ethylene glycol monoethylether.

By operating under the conditions described above, the system shown in FIG. 1 fed over 500 hours of continuous running with 3780 g of racemic n-propoxyethyl-[2-(6-methoxy-2-naphthyl)] propionate, yielded 632 g of S(+) 2-(6-methoxy-2-naphthyl) propionic acid with a conversion of 23%, having m.p. 154°-5° C. and $[\alpha]_D^{20}$ (C=1), (CHCl$_3$), +65.1°, and 2910 g of ester enriched with the R(−) form, without showing any perceptible decrease in effectiveness and productivity.

Racemization of N-Propoxyethyl-[2-(6-Methoxy-2-Naphthyl)] Propionate 100 g of n-propoxyethyl-[2-(6-methoxy-2-naphthyl)] propionate enriched with the R(−) form were added to a mixture of 100 g of ethylene glycol monopropyl ether and 11 ml of a solution of KOH at 10%.

The mixture was reflux-heated over 5 hours.

When the reaction was over ($[\alpha]_D^{20}$ 0°) the ethylene glycol monopropylether was evaporated, treated with 300 ml of ethyl acetate, washed 3 times with 300 ml of water and dehydrated on sodium sulphate.

After evaporation of the solvent, 92 g of racemic n-propoxyethyl-[2-(6-methoxy-2-naphthyl)] propionate were obtained with a yield of 92%.

EXAMPLE 5

1 g of Lipase obtained from *Candida Cylindracea* (sold by Meito Sangyo Co. Ltd. Japan, type OF 360, 360,000 u/g) was immobilized on 25 g AMBERLITE ® XAD 7, as described in Example 1.

The resin was then pressed into a bioreactor consisting of a thermoregulated column having a diameter of 3 cm and a height of 30 cm.

The column was saturated with racemic n-butoxyethyl-[2-(6-methoxy-2-naphthyl)] propionate and then fed with a flow of 0.4 ml/h of the same ester and 30 ml/h of phosphate buffer pH 6.5 (0.15 N) at 35° C.

The mixture leaving the column was conveyed into a second adsorption column having a diameter of 3 cm and a height of 30 cm, filled with 50 g of pressed AMBERLITE ® XAD 4.

At the outlet from the second column, one obtained a buffer solution which could be recycled to feed the column bioreactor, after having brought the pH to 6.5, again by the addition of NaOH.

The acid in the S(+) form and the ester enriched with the R(−) form were extracted from the adsorption column and separated according to the same procedure as described above in Example 1.

By operating under the same conditions as described above, the system was fed in a continuous way over 600 hours with 252 g of racemic ester, thereby obtaining 52 g of S(+) 2-(6-methoxy-2-naphthyl) propionic acid with a conversion of 30% and with m.p. 154°-5° C. and $[\alpha]_D^{20}$ (C=1), CHCl$_3$), +66.7°, and 176 g of n-butoxyethyl-[2-(6-methoxy-2-naphthyl)] propionate enriched with the R(−) form.

EXAMPLE 6

1 g of Lipase obtained from *Candida Cylindracea* (sold by Meito Sangyo Co. Ltd. Japan, type OF 360, 360,000 u/g) was immobilized on 25 g of AMBERLITE ® XAD 7, by using the same procedure as described above in Example 1.

The immobilized enzyme was then introduced into a bioreactor consisting of a thermoregulated column having a diameter of 3 cm and a height of 30 cm.

The column was saturated with racemic isopropoxyethyl-[2-(6-methoxy-2-naphthyl)] propionate and then fed with a flow of 0.4 ml/h of the same ester and of 35 ml/h of phosphate buffer pH 6.5 (0.15 N) at 35° C.

By operating under these conditions the system was fed in a continuous way over 500 hours with 210 g of racemic ester, thereby obtaining 42 g of S(+) 2-(6-methoxy-2-naphthyl) propionic acid with a conversion of 27% and with m.p. 154°-5° C. and $[\alpha]_D^{20}$ (C=1, CHCl$_3$), +64.1°, and 150 g of isopropoxyethyl-[2-(6-methoxy-2-naphthyl)] propionate enriched with the R(−) form.

EXAMPLE 7

5 g of Lipase obtained from *Candida Cylindracea* (sold by Meito Sangyo Co. Ltd. type OF 360, 360,000 u/g) were immobilized on 25 g of AMBERLITE ® XAD 7, by using the same procedure as described above in Example 1.

The immobilized enzyme was then introduced into a bioreactor consisting of a thermoregulated column having a diameter of 3 cm and a height of 30 cm.

The column was saturated with racemic polyethylenoxyethyl-[2-(6-methoxy-2-naphthyl)] propionate having M.W. of about 550 and wherein, in the polyethyleneoxyethyl group having formula —(CH$_2$CH$_2$O)-$n$—R$_2$, n is 11-13 and R$_2$ is CH$_3$, and subsequently, said column was fed with a flow of 0.4 ml/h of the same ester and of 35 ml/h of phosphate buffer pH 6.5 (0.15 N) at 35° C.

By operating under these conditions the system was fed in a continuous way over 600 hours with 264 g of racemic ester, thereby obtaining 23 g of S(+) 2-(6-methoxy-2-naphthyl) propionic acid with a conversion of 30% and with m.p. 153°–4° C. and $[\alpha]_D^{20}$ (C=1, CHCl$_3$), +63.9°, and 180 g of polyethyleneoxyethyl-[2-(6-methoxy-2-naphthyl)] propionate enriched with the R(−) form.

EXAMPLE 8

1 g of Lipase obtained from *Candida Cylindracea* (sold by Meito Sangyo Co. Ltd. Japan, type OF 360, 360,000 u/g) was immobilized on 25 g of AMBERLITE® XAD 7, as described in above in Example 1.

The immobilized enzyme was then introduced into a bioreactor consisting of a thermoregulated column having a diameter of 3 cm and a height of 30 cm.

The column was saturated with racemic phenoxyethyl-[2-(6-methoxy-naphthyl)] propionate and then fed with a flow of 0.3 ml/h of the same ester and of 30 ml/h of phosphate buffer pH 6.5 (0.15 N) at 40° C.

By operating under these conditions the system was fed in a continuous way over 300 hours with 98 g of a racemic ester, thereby obtaining 15 g of S(+) 2-(6-methoxy-2-naphthyl) propionic acid with a conversion of 23% and with m.p. 154°–5° C. and $[\alpha]_D^{20}$ (C=1, CHCl$_3$), +65.7, and 70 g of phenoxyethyl-[2-(6-methoxy-2-naphthyl)] propionate enriched with the R(−) form.

EXAMPLE 9 (REFERENCE)

Four tests of continuous enzymatic hydrolysis were carried out by operating exactly under the same conditions as described above in Example 2, while using, as carriers to immobilize the enzyme, instead of AMBERLITE® XAD 7, the following resins:

AMBERLITE® XAD 2, an adsorbent resin having a polymeric styrene/divinylbenezene matrix.

DUOLITE® ES 762, an adsorbent resin having a polymeric phenol/formaldehyde matrix, DUOLITE® S 761, an adsorbent resin having a polymeric phenol/formaldehyde matrix, DUOLITE® ES 468, an ion exchange resin having polyacrylic matrix, all of them having a porosity ranging from 50 to 1000 Å and a granulometry ranging from 1 to 0.01 mm.

In each test conversions were obtained of racemic ethoxyethyl-[2-(6-methoxy-2-naphthyl)] propionate into optical isomer S(+) of 2-(6-methoxy-2-naphthyl) propionic acid, below 5%.

What is claimed is:

1. A continuous process for the biotechnological preparation of optical isomer S(+) of 2-(6-methoxy-2-naphthyl) propionic acid consisting essentially of the reaction of a racemic (R,S) ester of 2-(6-methoxy-2-naphthyl) propionic acid having a melting point below 50° C., of formula:

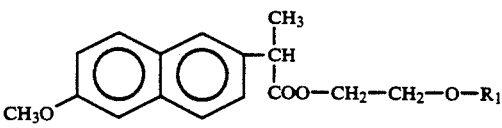

wherein R$_1$ is selected from the group consisting of alkyl radicals having from 2 to 10 carbon atoms, cycloalkyl radicals having from 4 to 6 carbon atoms, phenyl, tetrahydropyranyl, tetrahydrofuranyl radicals, —(CH$_2$CH$_2$O)$_n$—R$_2$ group, wherein n is a number ranging from 2 to 15 and R$_2$ is an alkyl radical having from 1 to 4 carbon atoms, with Lipase obtained from *Candida Cylindracea*, at temperatures ranging from 20° to 60° C. and at a pH ranging from 5 to 8, and in recovering said S(+) acid, characterized in that said ester is fed in a continuous way, together with a phosphate buffer solution, into a column bioreactor filled with said Lipase immobilized on a porous carrier consisting of polyacrylester Amberlite® XAD 7 or Amberlite® XAD 8 resins, having a porosity ranging from 50 to 1000Å and a granulometry ranging from 1 to 0.01 mm, wherein the ratio by weight Lipase/carrier ranges from 1:2 to 1:10.

2. A process according to claim 1, wherein the starting ester is racemic (R,S) ethoxyethyl-[2-(6-methoxy-2-naphthyl)] propionate.

3. A process according to claim 1, wherein the starting ester is racemic (R,S) n-propoxyethyl-[2-(6-methoxy-2-naphthyl)] propionate.

4. A process according to claim 1, wherein the starting ester is racemic (R,S) isopropoxyethyl-[2-(6-methoxy-2-naphthyl)] propionate.

5. A process according to claim 1, wherein the starting ester is racemic (R,S) n-butoxyethyl-[2-(6-methoxy-2-naphthyl)] propionate.

6. A process according to claim 1, wherein the temperature ranges from 30° to 50° C., and the pH ranges from 6 to 7.

7. A continuous process for the biotechnological preparation of optical isomer (S+) of 2-(6-methoxy-2-naphthyl) propionic acid consisting essentially of the reaction of a racemic (R,S) ester of 2-(6-methoxy-2-naphthyl) propionic acid having a melting point below 50° C., of formula:

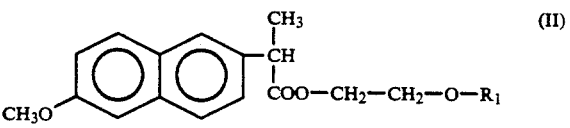

wherein R$_1$ is selected from the group consisting of alkyl radicals having from 2 to 10 carbon atoms, cycloalkyl radicals having from 4 to 6 carbon atoms, phenyl, tetrahydropyranyl, tetrahydrofuranyl radicals, —(CH$_2$CH$_2$O)$_n$—R$_2$ group, wherein n is a number ranging from 2 to 15 and R$_2$ is an alkyl radical having from 1 to 4 carbon atoms, with the Lipase obtained from *Candida Cylindracea*, at temperatures ranging from 20° to 60° C. and at a pH ranging from 5 to 8, and in recovering said S(+) acid, continuously supplying said ester together with a phosphate buffer solution, into a column bioreactor filled with said Lipase immobilized on a porous carrier consisting of polyacrylester AMBERLITE® XAD 8 or AMBERLITE® XAD 7 resins, said porous carrier having a porosity ranging from 50 to 1000 Å and a granulometry ranging from 1 to 0.01 mm, and wherein the ratio by weight Lipase/carrier ranges from 1:2 to 1:10.

* * * * *